US00PP08212P

United States Patent [19]

Chislett

[11] Patent Number: Plant 8,212

[45] Date of Patent: Apr. 27, 1993

[54] "CHISLETT SUMMER NAVEL" ORANGE TREE

[76] Inventor: Gregory J. K. Chislett, Via Piangil, Kenley, Victoria, 3497, Australia

[21] Appl. No.: 682,529

[22] Filed: Apr. 9, 1991

[51] Int. Cl.[5] ..... A01H 5/00

[52] U.S. Cl. ..... Plt./45

[58] Field of Search ..... Plt./45

[56] References Cited

U.S. PATENT DOCUMENTS

P.P. 347 11/1939 Workman ..... Plt. 45
P.P. 6,047 12/1987 Nieuwoudt ..... Plt. 45
P.P. 6,733 4/1989 Powell et al. ..... Plt. 45
P.P. 7,342 10/1990 Barnfield ..... Plt. 45
P.P. 7,651 9/1991 McLaren ..... Plt. 45

*Primary Examiner*—James R. Feyrer
*Attorney, Agent, or Firm*—Worrel & Worrel

[57] ABSTRACT

A new and distinct variety of navel orange tree which is somewhat remotely similar to the "Late Lane Navel" orange tree with which it is most closely related but from which it is distinguished by producing fruit which are mature for harvesting and shipment in early September holding on the tree until the end of April at Kenley, Victoria, Australia and which produces a higher internal flesh and external rind quality and color than comparable varieties.

1 Drawing Sheet

BACKGROUND OF THE NEW VARIETY

The present invention relates to a new and distinct variety of orange tree which will hereinafter be denominated varietally as "Chislett Summer Navel" orange tree and more particularly to an orange tree which produces fruit which are mature for harvesting and shipment approximately early spring in Kenley, Victoria, Australia and which further is distinguished principally as to novelty by producing large fruit which hang on the tree longer and with a higher internal flesh and external rind quality and color than the fruit of the "Late Lane Navel" orange tree.

The development of new varieties of citrus trees has not been as extensive as in the case of other families of fruit trees. In the United States, for example, while the sweet orange, known botanically as "Citrus sinensis", is typically a greater producer of fresh fruit by volume than any other fruit tree, the number of different varieties in production is significantly less than that of many other families of fruit trees. By way of illustration only, in the case of peach trees, the *Register of New Fruit and Nut Varities,* Second Edition, by Reid M. Brooks and H. P. Olmo, 1972, lists more than seven hundred varieties of peach trees in contrast to the just more than fifty varieties of orange trees. This disparity results, in part, from the susceptibility of many varieties of orange trees to diseases which are present in most of the citrus producing countries of the world. The infectious diseases are caused by bacteria, fungi and viruses and may, depending upon the specific type of disease, infect all portions of the trees. Accordingly, developmental work may be limited because of the prospect from expending enormous effort and time in the development of a new variety only ultimately to discover its susceptibility to a particular disease which destroys any significant commercial value therefor.

In any case, because of the comparative dearth of new varieties of orange trees, the discovery of new varieties having characteristics superior to those of known commercial varieties or having desirable ripening periods and a commercially acceptable resistance to disease is of event greater significance than in the case of other families of fruit trees. Where in addition, for example, the ripening period for a new variety of orange tree offers the prospect of fruit of high quality or otherwise attractive attributes later in the year than had theretofore been available in fruit of an equivalent character, the new variety is of noteworthy importance. The "Chislett Summer Navel" orange tree is such a variety.

ORIGIN AND ASEXUAL REPRODUCTION OF THE NEW VARIETY

The orange tree of the present invention was discovered in 1986 by the inventor in a cultivated grove of eight year old "Washington Navel" orange trees on the inventor's property at Kenley, Victoria, Australia. The orange tree of the subject invention was believed to be a "Washington Navel" orange tree when planted with the other "Washington Navel" orange trees in the grove. However, at the time of the discovery of the instant variety it appeared to be a whole plant sport. As a consequence, it can now only be stated that the new variety was a sport of a Citrus sinensis tree of unknown parentage in that the sport was from the portion of the tree which had been produced by grafting unknown budwood into "Citrange" seedling rootstock and planted in 1979.

The new variety was asexually reproduced in 1987 by the inventor Gregory John Kendall Chislett by budding onto Citrange seedling rootstock. The asexually reproduced trees were retained in the nursery on the inventor's property at Kenley and observed since that time. The inventor has through such observation confirmed that the distinctive characteristics, hereinafter set forth, which caused the parent tree to have been selected have identically reproduced themselves in the asexually reproduced trees. Budwood of the instant variety was sent to the University of California, Riverside for testing in May, 1990, but no data is yet available to compare its characteristics when asexually reproduced and grown in the Northern Hemisphere.

SUMMARY OF THE NEW VARIETY

The "Chislett Summer Navel" orange tree is characterized as to novelty by producing a fruit which hangs on the tree considerably longer and later than the closest comparative variety, the "Late Lane Navel" orange tree. The new variety possesses a higher internal flesh and external rind quality and color than "Late Lane Navel" orange tree. The fruit produced by the "Chislett Summer Navel" orange tree is ripe for harvesting and shipment in September in Kenley, Victoria, Australia, or in other words, approximately early Spring in Australia in the Southern Hemisphere.

BRIEF DESCRIPTION OF THE DRAWING

The accompanying drawing is a color photograph consisting of two frames, the upper frame showing four fruit of the new variety, the first in bottom plan view showing the navel end portion thereof; the second in top plan view showing the stem end portion thereof, the third in side elevation; and the fourth sectioned transversely of the longitudinal axis thereof to show the flesh. The lower frame of the photograph shows typical foliage of the new variety.

DETAILED DESCRIPTION

Referring more specifically to the pomological details of this new and distinct variety of naval orange tree, the following has been observed under the ecological conditions prevailing at the field of origin which is located at Kenley, Victoria, Australia. All major color code designations are by reference to the *Dictionary of Color,* by Maerz and Paul, Second Edition, 1950. A "Hunter Colour Difference Meter" of Gardener Laboratories Inc. was also used where deemed appropriate to give an a/b ratio where "a" is a measure of redness and "b" is a measure of yellowness for quantitative estimation of color development.

TREE

Generally:

*Size.*—For a ten year old tree, measurements taken from parent tree. Measurements taken from parent tree. Height — 3.1 meters (122.047 inches), diameter — 2.7 meters (106.299 inches).

*Figure.*—Normal upright growth. Attitude of branches at full flowering with no fruit on the tree is spreading. Significantly more vigorous and erect than a "Washington Navel" orange tree and noticeably more vigorous than a "Late Lane Navel" orange tree.

*Productivity.*—Good compared to the surrounding "Washington Navel" orange trees in the field of origin with higher yields than "Washington Navel" orange tree in the early years after planting due to greater tree size. Approximate yield is 125 Kg of fruit per tree in the case of a twelve year old tree on "Citrange" rootstock.

Trunk:

*Size.*—Measurements subject to variation due to horticultural practices including pruning. Information gathered from parent tree. Height to first branch — 30.5 cm (12.00 inches). Circumference — 40.0 cm (15.748 inches).

*Surface texture.*—Smooth bark characteristics normal for navel orange tree.

*Color.*—Brown (7A8) and light brown (11C2).

*Lenticels.*—Number — Approximately 15 per square cm (0.155 square inch). Size — Approximately 1.0 mm (0.039 inches) diameter.

Branches:

*Generally.*—The new variety is a spreading branched variety which is more erect than the "Late Lane Navel" orange tree and significantly more erect than the "Washington Navel" orange tree. The height to diameter ratio for a three year old tree of the new varieth is 1.26. The height to diameter ratio of the "Late Lane Navel" orange tree is 1.17. The height of the new variety is 2.35 meters as compared to 1.91 meters for the "Late Lane Navel" orange tree in three year old trees. Branch density is somewhat less than in the case of the "Washington Navel" orange tree and thus the new variety is a more open tree and similar in branch density to the "Late Lane Navel" orange tree.

*Size.*—Length — 53.5 cm (21.06 inches); 62.0 cm (24.40 inches); 29.0 cm (11.41 inches). Ancillary branches generally 30 cm (11.81 inches) to 70 cm (27.55 inches) long with many sub branches of shorter length leading to new growth producing fruit and flowers. Diameter — 21.5 cm (8.46 inches); 17.5 cm (6.88 inches); 13.0 cm (5.11 inches).

*Surface texture.*—Same surface texture as trunk.

*Color.*—One year or older wood — Brown (7A8) plus light brown (11C2). Immature branches — Green (16L1).

*Lenticels.*—Number — Approximately 14 per square cm (0.155 square inch). Size — Approximately 0.5 mm (0.019 inches) in diameter.

*Thorns.*—Thorns are present on juvenile and mature wood but are mainly present on water shoots. The variety is not considered "thorny" with the extent of thorniness being slightly more than in the case of the "Washington Navel" orange tree and similar to that of the "Late Lane Navel" orange tree.

LEAVES

Generally: Leaves are concave and, undulated, but not excessively so, with medium firmness of leaf blade. Petiole wings are rudimentary in development with a 2.67 mm (0.105 inches) width. This is significantly different (P=0.05) from other late navel varieties except "Late Lane Navel" in 1991. The widths of the petiole wings in other varieties of orange trees were, respectively, as follows: "Powell" orange tree — 2.35 mm (0.093 inches); "Barnfield" orange tree — 2.28 mm (0.090 inches); "Rhode" orane tree — 2.38 mm (0.094 inches); "Summer Gold" orange tree — 2.99 mm (0.118 inches); "Autumn Gold" orange tree — 2.37 mm (0.093 inches) and "Late Lane Navel" orange tree — 2.39 mm (0.094 inches).

Size:

*Generally.*—Medium to small. Simple leaves with reticulate veination.

*Average length.*—Mean approximately 10.95 cm (4.311 inches). Range 9.00 cm (3.543 inches) to 15.00 cm (5.905 inches).

*Average width.*—Mean approximately 5.31 cm (2.090 inches). Range 3.20 cm (1.259 inches) to 6.40 cm (2.519 inches).

Shape: Elliptical.

*Base.*—Acute.

*Apex.*—Attenuate.

Color:

*Upwardly disposed surface.*—Green (22H6). Immature leaves Green (21L7).

*Downwardly disposed surface.*—Green (21I2). Immature leaves Green (20H3).

Marginal form:

*Generally.*—Entire to slightly sinuate.

Glandular characteristics: Dotted over underside. Stomata approximately 146 per square cm (0.155 square inch).

Petiole:

*Length.*—Approximately 1.68 cm (0.661 inches). Range 0.70 cm (0.275 inches) to 3.4 cm (1.338 inches).

*Thickness.*—Approximately 3.79 mm (0.149 inches). Range 0.60 mm (0.023 inches) to 5.0 mm (0.196 inches).

Stem glands: None observed.

Stipules: None observed.

Leaf aroma: Has a distinctly more volatile and stronger aroma, which is "lemony" in character, in contrast to that of the "Washington Navel" orange tree which is sweeter, while that of the "Late Lane Navel" orange tree is "grassy" in character.

FLOWERS

Flower buds:

*Size.*—Length approximately 1.46 cm (0.574 inches). Range 1.0 cm (0.393 inches) to 1.8 cm (0.708 inches). Diameter approximately 0.25 mm (0.364 inches). Range 5.0 mm (0.196 inches) to 12.0 mm (0.472 inches).

*Shape.*—Elliptical.

*Petiole.*—Length approximately 7.95 mm (0.312 inches). Range 6.0 mm (0.236 inches) to 10.0 mm (0.393 inches).

*Color.*—White (9D1).

Flowers:

*Date of first bloom.*—Oct. 4, 1989 in Kenley, Victoria, Australia.

*Size.*—Generally — Same as bud petiole lengths.

*Petiole.*—Five sided glabrous, corresponding to each sepal.

*Petals.*—Number — 5 fleshy, alternate to sepals. Color — White (9D1). Size — Approximate length 1.35 cm (0.531 inches). Range 1.0 cm (0.393 inches) to 1.54 cm (0.606 inches). Approximate diameter 0.45 cm (0.177 inches). Range 0.35 cm (0.137 inches) to 0.50 cm (0.196 inches).

*Stamens.*—Number — medium Approximately 25. Range 23 to 28. Style — Development is complete.

*Anthers.*—Number — Approximately 25. Range 23 to 27. Color — Pale yellow (RHS grey-yellow 162A and 162B.

*Pistil.*—Ovary locule number — 12 carpellary. Range 10 to 14. Axile placentation, 1-2 ovules per ovary. Hypogynous receptacle. Disc present.

*Pollen.*—No viable pollen is present.

Inflorescences: Appear as single terminal flowers and as clusters.

FRUIT

Maturity when described: Ripe for commercial harvesting and shipment approximately mid Spring holding until mid Autumn in Kenley, Victoria, Australia in the Southern Hemisphere. Harvest period lasting exceptionally long when compared with other varieties extending from early August to the end of April in the following calendar year in Kenley, Victoria, Australia. Earliest measurement September, 1988 (15.1 sugar/acid ration).

Comparison with other varieties: Large, although smaller than "Washington Navel" orange tree at full color. For example, average diameter is 73.4 mm (2.89 inches) compared to 76.4 mm (3.01 inches) for "Washington Navel" orange tree in late July. Intra-fruit size and shape uniformity in late July is higher than for "Washington Navel" orange tree. Fruit is of high quality commercial grade of oblate to globose overall shape. This compares with the shapes of the fruit of other varieties of orange trees as follows: "Late Lane Navel" orange tree — globose to ovoid; "Powell" orange tree — oblate to ovovoid; "Barnfield" orange tree — oblate to globose; "Rhode" orange tree — globose to ovoid; "Summer Gold" orange tree — globose to ovoid; and "Autumn Gold" orange tree — globose to ovoid. Shape of distal end is truncated to slightly nippled with basal end truncate to moderately depressed. The columella is small at 6.5 mm (0.256 inches) average compared to other late navel varieties and is semi-hollow to solid in structure. The fruit of the "Late Lane Navel" orange tree is semi-hollow.

Size:

*Generally.*—Average to good size. Similar to fruit of "Late Lane Navel" orange tree.

*Latitudinal fruit diameter.*—Approximately 83.18 mm (3.274 inches). Ranging from 70.1 mm (2.759 inches) (early Spring 1989) to 88.5 mm (3.484 inches) (measured Mar. 15, 1989 in Autumn).

*Longitudinal fruit diameter.*—Approximately 86.96 mm (3.423 inches). Ranging from 72.0 mm (2.834 inches) (early Spring 1989) to 90 mm (3.543 inches) (measured Mar. 15, 1989 in Autumn).

*Form.*—Uniformity — Good.

*Seeds.*—None.

| Form-Symmetry-Height to width ratio | Date |
|---|---|
| 1.008 | November 4, 1988 |
| 0.996 | December 12, 1988 |
| 1.012 | February 14, 1989 |
| 1.016 | March 15, 1989 |
| 1.031 | April 18, 1989 |
| 1.024 | September 15, 1989 |
| **Fruit Stem End Depression Height** | **Date** |
| 2.6 mm (.102 inches) | November 4, 1988 |
| 4.0 mm (.157 inches) | December 12, 1988 |
| 4.5 mm (.177 inches) | February 14, 1989 |
| 4.9 mm (.193 inches) | March 15, 1989 |
| 5.4 mm (.212 inches) | April 18, 1989 |
| **Fruit External Navel Diameter** | **Date** |
| 5.4 mm (.212 inches) | November 4, 1988 |
| 6.7 mm (.236 inches) | December 12, 1988 |
| 4.5 mm (.177 inches) | February 14, 1989 |
| 5.9 mm (.232 inches) | March 15, 1989 |
| 4.9 mm (.193 inches) | April 18, 1989 |
| **Fruit Individual Mass** | **Date** |
| 266.7 g (9.33 oz) | November 4, 1988 |
| 307.9 g (10.77 oz) | December 12, 1988 |
| 350.8 g (12.27 oz) | February 14, 1989 |
| 345.8 g (12.10 oz) | March 15, 1989 |
| 335.8 g (11.75 oz) | April 18, 1989 |

*Stem.*—Length — Approixmately 8.0 mm (0.314 inches). Range 6.8 mm (0.267 inches) to 11.2 mm (0.441 inches). Thickness — Approximately 3.9 mm (0.153 inches). Range 3.1 mm (0.122 inches) to 6.0 mm (0.236 inches).

Skin:

| Thickness - Neck End Rind | Date |
|---|---|
| 6.0 mm (.236 inches) | November 4, 1988 |
| 8.3 mm (.326 inches) | December 12, 1988 |
| 8.4 mm (.330 inches) | February 14, 1989 |
| 10.7 mm (.421 inches) | March 15, 1989 |
| 10.4 mm (.409 inches) | April 18, 1989 |

| Equatorial Rind Thickness | Date |
|---|---|
| 4.7 mm (.185 inches) | November 4, 1988 |
| 5.3 mm (.208 inches) | December 12, 1988 |
| 5.8 mm (.228 inches) | February 14, 1989 |
| 6.3 mm (.248 inches) | March 15, 1989 |
| 5.5 mm (.216 inches) | April 18, 1989 |

| Navel End Rind Thickness | Date |
|---|---|
| 3.2 mm (.125 inches) | November 4, 1988 |
| 3.4 mm (.133 inches) | December 12, 1988 |
| 3.9 mm (.153 inches) | February 14, 1989 |
| 3.8 mm (.149 inches) | March 15, 1989 |
| 3.6 mm (.141 inches) | April 18, 1989 |

*Rind texture.*—Significantly fine and smooth compared to that of the "Washington Navel" orange tree and detectably smoother than that of the "Late Lane Navel" orange tree when compared on the inventor's property. Rind texture can be extremely smooth on the navel end with a high lustre graduating to slightly pebbled at the stem end. Rind texture on a 0 to 5 scale where 1=smooth and 5=rough. Average 2.72 smooth compared to the standards of "Washington Navel" orange tree and "Valencia" orange tree. 5 to 7 latitudinal grooves radiating from the neck end.

*Rind color.*—Color in October is Orange (RHS 24a) and is the same as that of the "Late Lane Navel" orange tree, being more yellow and lighter colored than that of the "Washington Navel" orange tree. The new variety attained full orange color approximately four weeks later than that of the "Washington Navel" orange tree and at least two weeks after "Late Lane Navel" orange tree. Color break is in mid-May with complete coloration occurring by mid-July in North Western Victoria (Kenley, Australia). a.b. ratio — 0.24 in Autumn in Australia — Apr. 18, 1989. Orange (10H10) in Spring in Australia — Oct. 13, 1989.

*Handling quality.*—Excellent. Skin is hard which makes it excellent for handling.

*Peeling characteristics.*—The rind is hard with medium adherence to the flesh which makes it more difficult to peel than the fruit of the "Washington Navel" orange tree and is similar in this respect to that of the "Late Lane Navel" orange tree.

*Regreening.*—Regreening is not severe, but does occur somewhat beginning in December and January varying from year to year and is similar to the regreening of "Valencia" orange tree, although not as severe. "Late Lane Navel" orange trees appear to regreen more than the instant variety. Regreening usually disappears after April. The tendency to maintain an orange color during on-tree storage is greater than other late naval varieties and is the only late navel to maintain a color more orange than green (a positive Hunter a/b ratio) throughout two consecutuve seasons. Fruit of the "Washington Navel" orange tree does not store on the tree long enough to regreen. Rind puffing with on-tree storage is not excessive and if fruit is not large at maturity resistance to puffing is high. Tendency to puff is less than that of the "Late Lane Navel" orange tree.

*Oil glands.*—Oil glands are conspicuous with medium density of 40.6 glands per 25 $mm^2$ compared to "Late Lane Navel" orange tree having 44.4 glands per 25 $mm^2$.

*Navel.*—The navel is always present and is always visible, moderately protruding, but not prominant. Diameter is 1.4 mm (0.055 inches) to 17.1 mm (0.673 inches).

*Albedo.*—Color of the albedo is white. Less albedo intrusion between segments than in the case of the "Washington Navel" orange tree and "Late Lane Navel" orange tree. The number of segments ranges from 9.0 to 12.0 with a mean of 11.2 compared to "Late Lane Navel" orange tree at a mean of 10.2. Segment to Segment adhesion is greater than for "Late Lane Navel" orange tree and much greater than for "Washington Navel" orange tree.

| Fruit Softness - Deformation from 2 Kg force | Date |
|---|---|
| 4.2 mm (.165 inches) | November 4, 1988 |
| 3.5 mm (.137 inches) | December 12, 1988 |
| 4.9 mm (.192 inches) | February 14, 1989 |
| 4.2 mm (.165 inches) | March 15, 1989 |
| 5.7 mm (.224 inches) | April 18, 1989 |

*Flesh color.*—Orange (9L9) in Spring of Australia, 1989.

*Juice.*—The juice content is high and ranged from 51.8% to 55.9% in 1989 and juice citric acid content ranged from 0.40 to 0.57 g/100 ml in 1989, decreasing over the season.

*Juice flavor.*—Very sweet and pleasant and after November does not embitter on storage due to a low limonin concentration. The Sugar to Acid Ratio is high, increasing from 15.1 to 32.6 over the season from September to March, 1988/89 at Kenley, Australia. The fruit and juice, therefore, tastes less acidic and sweeter as the season progresses, but always remains attractive. The fruit has no areola and the style is not persistent. The pulp vesicles are large and long with less random orientation than in the case of the "Late Lane Navel" orange tree and very juicy.

| Juice - Percent Juice Content | Date |
|---|---|
| 55.9 Percent | November 4, 1988 |
| 55.6 Percent | December 12, 1988 |
| 52.1 Percent | February 14, 1989 |
| 51.8 Percent | March 15, 1989 |
| 51.8 Percent | April 18, 1989 |

| Juice - Citric Acid Content in Grams per 100 Millimeters: | Date |
|---|---|
| 0.57 (g/100 ml) | November 4, 1988 |
| 0.50 (g/100 ml) | December 12, 1988 |
| 0.37 (g/100 ml) | February 14, 1989 |
| 0.35 (g/100 ml) | March 15, 1989 |
| 0.40 (g/100 ml) | April 18, 1989 |

| Juice - Sugar Content in Degrees Brix: | Date |
|---|---|
| 13.1 | November 14, 1988 |
| 12.2 | December 12, 1988 |
| 11.2 | February 14, 1989 |
| 11.4 | March 15, 1989 |

-continued

| | |
|---|---|
| 11.4 | April 18, 1989 |
| Juice - Sugar to Acid Ratio: | Date |
| 15.1 | September 16, 1988 |
| 19.4 | October 11, 1988 |
| 23.0 | November 4, 1988 |
| 24.4 | December 12, 1988 |
| 30.3 | February 14, 1989 |
| 32.6 | March 15, 1989 |
| 28.5 | April 18, 1989 |
| Total Soluble Solids in Kilograms per Metric Ton: | Date |
| 73.8 Kg/tonne | November 4, 1988 |
| 68.4 Kg/tonne | December 12, 1988 |
| 58.7 Kg/tonne | February 14, 1989 |
| 59.4 Kg/tonne | March 15, 1989 |
| 59.5 Kg/tonne | April 18, 1989 |

(Tonne: a Metric Ton: 1,000 Kilograms)

*Flavor.*—No off flavors were detected. Non limonin bitter taste was detected.

*Aroma.*—Noteworthy.

*Ripening.*—Even and very late.

*Eating quality.*—Very noteworthy.

*Resistance to fruit drop.*—Considered high for a late navel variety. Although slight fruit drop can occur beginning in late November, most of this is due to slight splitting from the navel or some other damage. Approximately 70% of fruit remains on the tree until April, seven months after maturity. A significant amount of fruit can hang for more than twelve months after maturity, as will fruit of "Valencia" orange trees, although resistance to drop is not as high as for "Valencia" orange trees. The resistance to fruit drop of the instant variety is higher than in the case of the "Late Lane Navel" orange tree as most will not hang after the end of November. "Summer Gold" orange trees fall heavily by November in North Western Victoria, Australia.

Although the new variety of navel orange tree possesses the described characteristics noted above as a result of the growing conditions prevailing in Kenley, Victoria, Australia it is to be understood that variations of the usual magnitude and characteristics incident to changes in growing conditions, fertilization, pruning, pest control and other horticultural practices are to be expected.

Having thus described and illustrated my new variety of navel orange tree, what I claim as new and desire to be secured by Plant Letters Patent is:

1. A new and distinct variety of navel orange tree substantially as illustrated and described and which is somewhat remotely similar to the "Late Lane Navel" orange tree with which it is most closely similar, but from which is distinguished and characterized principally as to novelty by producing fruit which are mature for commercial harvesting and shipment in early September and which holds on the tree until the end of April of the following year in Kenley, Victoria, Australia and which possesses a higher internal flesh and external rind quality and color than comparable varieties.

* * * * *

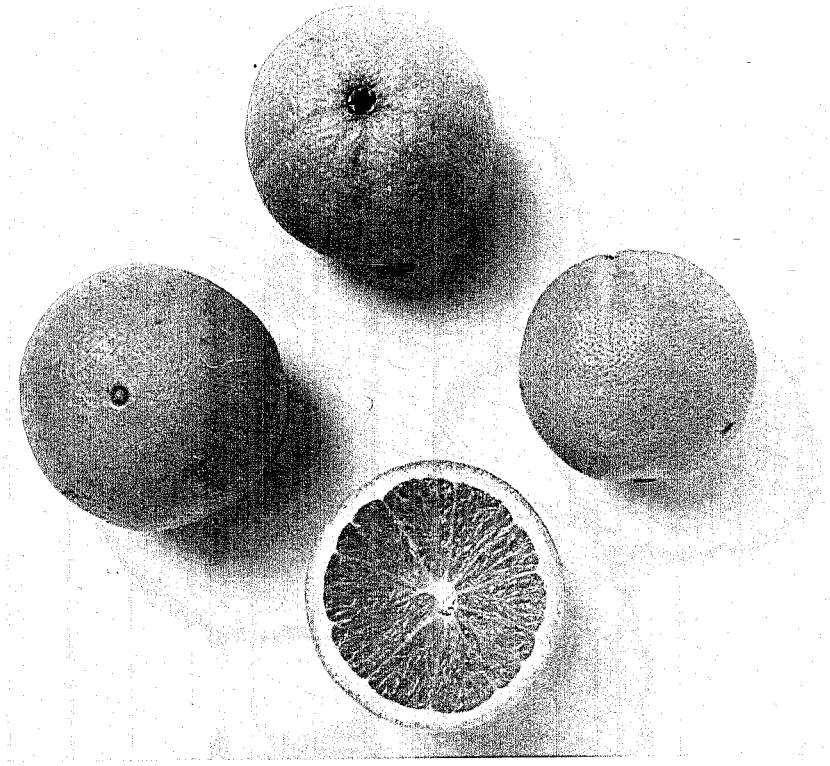
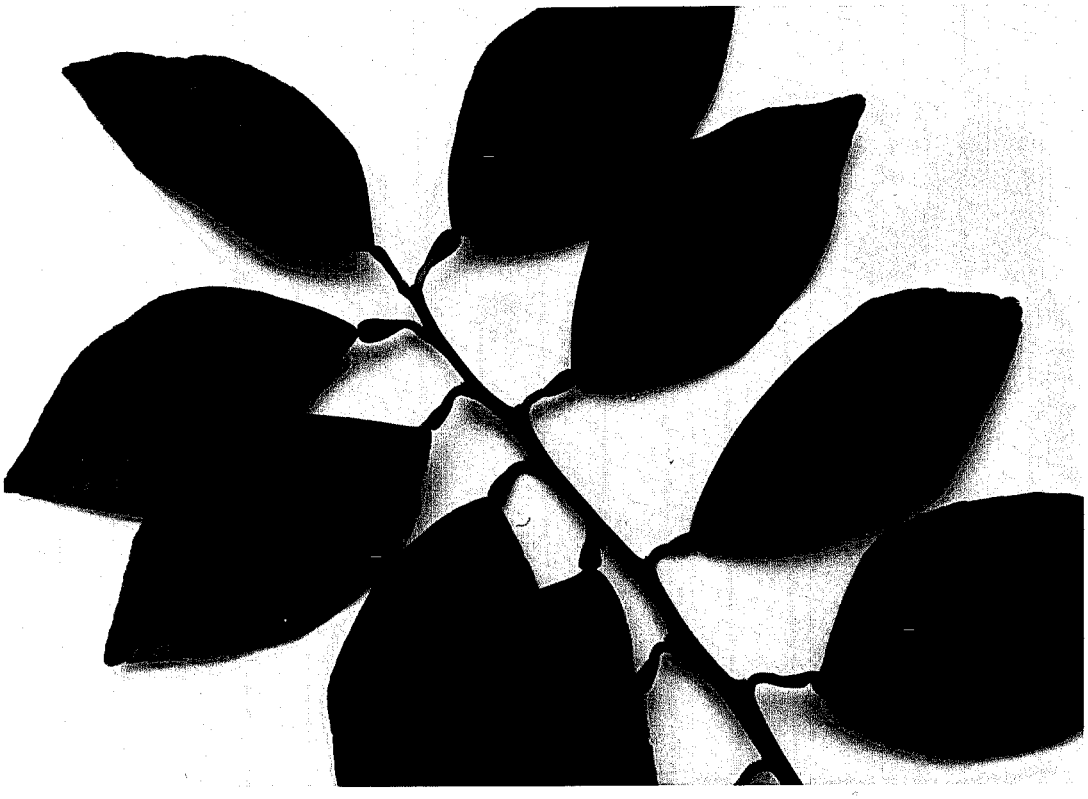

UNITED STATES PATENT AND TRADEMARK OFFICE

CERTIFICATE OF CORRECTION

PLANT PATENT NO. : PP: 8,212

DATED : April 27, 1993

INVENTOR(S) : GREGORY J.K. CHISLETT

It is certified that error appears in the above-identified patent and that said Letters Patent is hereby corrected as shown below:

On the title page, Item

(76) Inventor: delete "3497" and substitute ---3597--- .

Signed and Sealed this

Twenty-eighth Day of December, 1993

*Attest:*

Bruce Lehman

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : Plant 8,212

DATED : April 27, 1993

INVENTOR(S) : GREGORY J.K. CHISLETT

It is certified that error appears in the above-identified patent and that said Letters Patent is hereby corrected as shown below:

Column 4, line 6, delete "varieth" and substitute ---variety---.

line 49, delete "orane" and substitute ---orange---.

Column 5, line 27, delete "0.25" and substitute ---9.25---.

Column 6, line 14, delete "ovovoid" and substitute ---obovoid---.

Column 9, line 19, delete "Non" and substitute ---No---.

Signed and Sealed this

First Day of February, 1994

Bruce Lehman

*Attest:*

BRUCE LEHMAN

*Attesting Officer*

*Commissioner of Patents and Trademarks*